(12) United States Patent
Vaez-Iravani et al.

(10) Patent No.: US 9,068,917 B1
(45) Date of Patent: Jun. 30, 2015

(54) SYSTEMS AND METHODS FOR INSPECTION OF A SPECIMEN

(75) Inventors: Mehdi Vaez-Iravani, Los Gatos, CA (US); Eliezer Rosengaus, Palo Alto, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 2237 days.

(21) Appl. No.: 11/374,711

(22) Filed: Mar. 14, 2006

(51) Int. Cl.
*G01N 21/00* (2006.01)
*G01N 21/88* (2006.01)

(52) U.S. Cl.
CPC .............. *G01N 21/00* (2013.01); *G01N 21/88* (2013.01); *G01N 2021/8825* (2013.01)

(58) Field of Classification Search
CPC .......... G01N 21/8806; G01N 21/9501; G01N 21/95607; G01N 2021/479; G01N 2021/8825; G01N 2021/95676; G01N 2201/06113; G02B 17/0808; G02B 17/0856; G02B 17/0892; G02B 21/04; G03F 7/70225
USPC ......................................................... 382/141
See application file for complete search history.

(56) References Cited

U.S. PATENT DOCUMENTS

| | | | | |
|---|---|---|---|---|
| 5,576,831 | A * | 11/1996 | Nikoonahad et al. | 356/623 |
| 6,208,411 | B1 * | 3/2001 | Vaez-Iravani | 356/237.2 |
| 6,738,505 | B1 * | 5/2004 | Prince | 382/150 |
| 2002/0080346 | A1 * | 6/2002 | Vaez-Iravani et al. | 356/237.2 |
| 2003/0025904 | A1 * | 2/2003 | Sakai et al. | 356/237.2 |
| 2004/0027688 | A1 * | 2/2004 | Lange | 359/726 |
| 2004/0095573 | A1 * | 5/2004 | Tsai et al. | 356/237.5 |
| 2004/0246476 | A1 * | 12/2004 | Bevis et al. | 356/237.5 |
| 2007/0146873 | A1 * | 6/2007 | Ortyn et al. | 359/386 |

OTHER PUBLICATIONS

U.S. Appl. No. 11/158,440 entitled Multi-Spot Illumination and Collection Optics for Highly Tilted Wafer Planes, filed Jun. 22, 2005.
U.S. Appl. No. 11/158,441 entitled Multi-Spot Illumination and Collection Optics for Highly Tilted Wafer Planes, filed Jun. 22, 2005.

* cited by examiner

*Primary Examiner* — Kim Vu
*Assistant Examiner* — Michael Vanchy, Jr.
(74) *Attorney, Agent, or Firm* — Ann Marie Mewherter (57) ABSTRACT

Systems and methods for inspection of a specimen are provided. One system includes an illumination subsystem configured to illuminate the specimen by scanning a spot across the specimen. The system also includes a non-imaging detection subsystem configured to generate output signals responsive to light specularly reflected from the spot scanned across the specimen. In addition, the system includes a processor configured to generate images of the specimen using the output signals and to detect defects on the specimen using the images. In one embodiment, the non-imaging detection subsystem includes an objective and a detector. An NA of the objective does not match a pixel size of the detector. In another embodiment, the non-imaging detection subsystem includes an objective having an NA of greater than about 0.05. The system may be configured for multi-spot illumination and multi-channel detection. Alternatively, the system may be configured for single spot illumination and multi-channel detection.

23 Claims, 6 Drawing Sheets

SYSTEMS AND METHODS FOR INSPECTION OF A SPECIMEN

BACKGROUND OF THE INVENTION

1. Field of the Invention

This invention generally relates to systems and methods for inspection of a specimen. Certain embodiments relate to an inspection system that includes a non-imaging detection subsystem configured to generate output signals responsive to light specularly reflected from a spot scanned across the specimen and a processor configured to generate images of the specimen using the output signals.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers to promote higher yield in the manufacturing process and thus higher profits. When inspecting specular or quasi-specular surfaces such as semiconductor wafers, bright field (BF) and dark field (DF) modalities are used. In BF inspection systems, collection optics are positioned such that the collection optics capture a substantial portion of the light specularly reflected by the surface under inspection. In contrast, in DF inspection systems, the collection optics are positioned out of the path of the specularly reflected light such that the collection optics capture light scattered by objects on the surface being inspected such as microcircuit patterns or contaminants on the surfaces of wafers.

In BF inspection systems such as the 2351 system that is commercially available from KLA-Tencor, San Jose, Calif., imaging optics are commonly used to direct the light specularly reflected from the surface being inspected to the surface of an imaging sensor (e.g., an array detector such as a charged coupled device (CCD) or photodiode array). The quality of the imaging optics is a crucial determinant of the image quality overall, and the imaging optics (e.g., the numerical aperture of the imaging optics) need to be carefully matched to the periodicity of the imaging detector (e.g., the periodicity of the detector pixels) to prevent sampling effects such as aliasing.

In DF inspection systems such as the AIT family of tools and the SP1 and SP2 tools that are commercially available from KLA-Tencor, an intense spot of light is commonly used (e.g., light generated by a monochromatic laser) to limit the extent (i.e., the area) of the surface being illuminated. The inspection systems are configured to collect scattered light from the surface under inspection using non-imaging optics (such as Fresnel lenses or curved mirrors) and to direct the collected light onto the surface of relatively large area sensors (such as photodiodes or photomultiplier tubes). The inspection systems are also configured to sequentially illuminate different regions of the surface under inspection by scanning the spot over the surface by either translating the surface under the optics of the inspection system or by steering the illumination beam using devices such as galvanometers, rotating polygonal mirrors, or acousto-optic deflectors. The DF inspection systems are configured to form a digital image by using knowledge of the position being illuminated at the time the sensor is sampled. Since the non-imaging or "acquisition" optics collect a substantially small portion of the light used for illumination, relatively intense light sources such as lasers are typically used in DF inspection systems to illuminate the spot on the surface under inspection such that sufficient photons can be collected to provide a sufficient signal-to-noise ratio for defect detection.

Some DF inspection systems are configured to scan multiple spots across the surface under inspection simultaneously. In such systems, a relatively sparse array of detectors can be used to increase the speed of data acquisition by parallelization. Such a system configuration requires somewhat more sophisticated imaging optics than single spot DF inspection systems, but the tolerances of the optics can be substantially relaxed from those used in bright field systems.

Accordingly, it would be advantageous to develop systems and methods for BF inspection of a specimen such as a wafer that can produce adequate quality images of the specimen without requiring high quality imaging optics, without matching the optics to the periodicity of the detector, and without causing sampling effects such as aliasing, that allows the use of optics having a relatively high numerical aperture to increase the efficiency of light collection, that allows the use of detectors having a relatively high gain, that is less expensive than other bright field inspection systems, or some combination thereof.

SUMMARY OF THE INVENTION

The following description of various system and method embodiments is not to be construed in any way as limiting the subject matter of the appended claims.

One embodiment relates to a system configured to inspect a specimen. The system includes an illumination subsystem configured to illuminate the specimen by scanning a spot across the specimen. The system also includes a non-imaging detection subsystem configured to generate output signals responsive to light specularly reflected from the spot scanned across the specimen. In addition, the system includes a processor configured to generate images of the specimen using the output signals and to detect defects on the specimen using the images.

In one embodiment, the non-imaging detection subsystem includes an objective and a detector. In one such embodiment, a numerical aperture (NA) of the objective does not match a pixel size of the detector. In another embodiment, the non-imaging detection subsystem includes an objective having an NA of greater than about 0.05. In some embodiments, the system is configured to alter a sampling frequency of the non-imaging detection subsystem to alter a magnification of the images. In a further embodiment, the system is configured to select a sampling frequency of the non-imaging detection subsystem to substantially eliminate aliasing effects in the images. In an additional embodiment, the non-imaging detection subsystem includes an avalanche photodiode or a photomultiplier tube.

In one embodiment, the illumination subsystem includes a narrowband light source. In a different embodiment, the illumination subsystem includes a broadband light source. In one such embodiment, the non-imaging detection subsystem is configured to simultaneously generate different output signals responsive to different wavelengths of the light specularly reflected from the spot scanned across the specimen. In a different such embodiment, each of the output signals is responsive to multiple wavelengths of the light specularly reflected from the spot scanned across the specimen.

In another embodiment, the illumination subsystem is configured to illuminate the specimen by flood illumination. In one such embodiment, the non-imaging detection subsystem includes an array of fibers configured to collect the light specularly reflected from different portions of the spot scanned across the specimen. In this manner, the system may be configured for flood illumination of the specimen and collection by an array of fibers. Such an embodiment is, therefore, configured for single spot illumination and multi-channel detection. In addition, the specimen may be flood illuminated, and the magnified image of the specimen may be projected onto an array of fibers, a two-dimensional array of non-imaging detectors, or a two-dimensional multi-channel array of a non-imaging detector.

In another embodiment, the processor is configured to perform automatic defect classification. In an additional embodiment, an accuracy of the system is substantially independent of variations in the specimen caused by variations in a process performed on the specimen prior to inspection. In a further embodiment, the processor is configured to determine if the defects are nuisance defects.

In one embodiment, the illumination subsystem includes a fiber configured to direct light from a light source to an objective. The objective is configured to focus light from the fiber onto the specimen and to control a size of the spot on the specimen. In a different embodiment, the illumination subsystem is configured to illuminate the specimen by scanning multiple spots across the specimen simultaneously. In one such embodiment, the non-imaging detection subsystem is configured to simultaneously generate output signals responsive to light specularly reflected from the multiple spots scanned across the specimen. In this manner, the system may be configured for multi-spot illumination and multi-channel detection.

In some embodiments, the system includes an additional non-imaging detection subsystem configured to generate additional output signals responsive to light scattered from the spot scanned across the specimen. In one such embodiment, the processor is configured to detect the defects on the specimen using the additional output signals. In another such embodiment, the non-imaging detection subsystem and the additional non-imaging detection subsystem are configured to generate the output signals and the additional output signals substantially simultaneously.

In another embodiment, the illumination subsystem is configured to illuminate the specimen by scanning multiple spots across the specimen simultaneously. In one such embodiment, the system includes an additional non-imaging detection subsystem configured to simultaneously generate additional output signals responsive to light scattered from the multiple spots scanned across the specimen, and the processor is configured to detect the defects on the specimen using the additional output signals. In another such embodiment, the additional non-imaging detection subsystem is configured to generate the additional output signals while the non-imaging detection subsystem is generating the output signals.

In some embodiments, the system includes an additional non-imaging detection subsystem configured to generate additional output signals responsive to light specularly reflected from the spot scanned across the specimen. In one such embodiment, the output signals and the additional output signals are responsive to light having different polarizations. In an additional embodiment, the specimen includes a patterned wafer or a non-patterned wafer. The non-patterned wafer may include a wafer having a film formed thereon, a bare silicon wafer, or a wafer having a resist formed thereon. Each of the embodiments of the system described above may be further configured as described herein.

Another embodiment relates to a system configured to inspect a specimen. This system includes an illumination subsystem configured to illuminate the specimen by scanning a spot across the specimen. The system also includes an objective configured to collect light specularly reflected from the spot scanned across the specimen. An NA of the objective is greater than about 0.05. In addition, the system includes a non-imaging detector configured to detect the light collected by the objective and to generate amplified output signals responsive to the detected light. The NA of the objective is not matched to a pixel size of the non-imaging detector. The system further includes a processor configured to generate images of the specimen using the amplified output signals and to detect defects on the specimen using the images. This system embodiment may be further configured as described herein.

An additional embodiment relates to a method for inspecting a specimen. The method includes illuminating the specimen by scanning a spot across the specimen. The method also includes generating non-image output signals responsive to light specularly reflected from the spot scanned across the specimen. In addition, the method includes generating images of the specimen using the non-image output signals. The method further includes detecting defects on the specimen using the images. This method embodiment may include any other step(s) described herein.

BRIEF DESCRIPTION OF THE DRAWINGS

Other objects and advantages of the invention will become apparent upon reading the following detailed description and upon reference to the accompanying drawings in which.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "specimen" refers to a wafer. As used herein, the term "wafer" generally refers to substrates formed of a semiconductor or non-semiconductor material.

Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include one or more layers formed upon a substrate. For example, such layers may include, but are not limited to, a resist, a dielectric material, and a conductive material. Many different types of such layers are known in the art, and the term wafer as used herein is intended to encompass a wafer including all types of such layers.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

Although embodiments are described herein with respect to wafers, it is to be understood that the systems and methods described herein may be used for inspection of any other specimen that would benefit from inspection that can be performed relatively quickly, relatively inexpensively, and to generate relatively moderate quality images of the specimen that can be used to detect defects on the specimen.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

Figure 1:
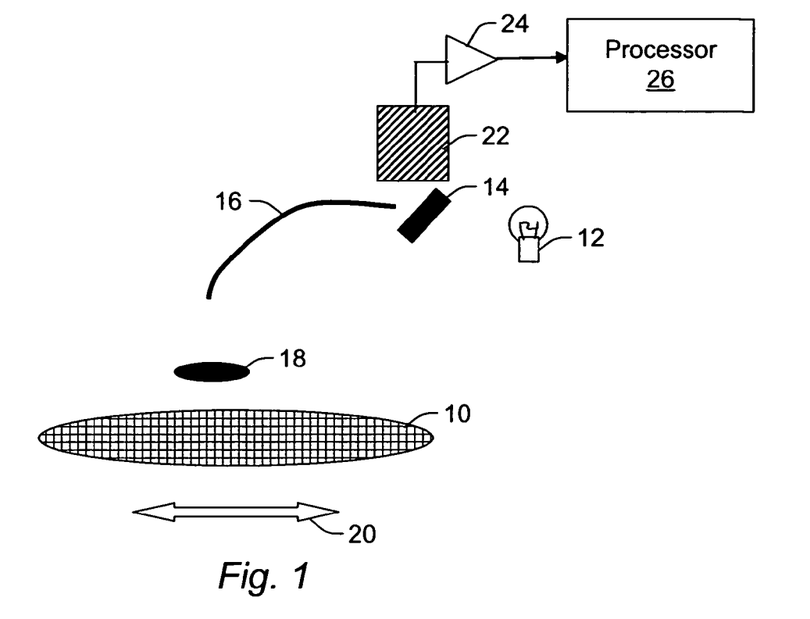
FIGS. 1-6 are schematic diagrams illustrating a side view of various embodiments of a system configured to inspect a specimen.

FIG. 1 illustrates one embodiment of a system configured to inspect a specimen (i.e., a surface under observation) such as a semiconductor wafer. The system includes an illumination subsystem configured to illuminate specimen 10 by scanning a spot across the specimen. For instance, the illumination subsystem includes light source 12. Light source 12 may be a narrowband light source in one embodiment. The narrowband light source may include any appropriate narrowband light source known in the art such as a laser. The narrowband light source may be configured to generate light having one or more selected characteristics such as wavelength and polarization. Light from light source 12 may be directed to beam splitter 14. Light from light source 12 that passes through beam splitter 14 may be directed to one or more optical components that are configured to direct the light to the specimen. Beam splitter 14 may include any appropriate beam splitter known in the art.

In one embodiment, the illumination subsystem includes fiber 16 configured to direct light from light source 12 to objective 18. Fiber 16 may include any suitable fiber known in the art. Objective 18 may include any appropriate objective known in the art. In addition, although objective 18 is shown in FIG. 1 as including one refractive lens, it is to be understood that the objective may include more than one refractive lens or one or more reflective optical components.

In one such embodiment, objective 18 is configured to focus light from fiber 16 onto specimen 10. The end of fiber 16 through which the illumination exits the fiber creates a virtual aperture, and the dimensions (e.g., diameter) of the end of the fiber establish the spatial extent of the illuminated spot. In addition, the objective may be configured to control a size of the spot on the specimen. In one such embodiment, the fiber may have a relatively large diameter (e.g., about 1 mm or larger). Therefore, light exiting fiber 16 may have a diameter of about 1 mm or larger. In addition, the objective may be configured to control the size of the illuminated spot on the surface of specimen 10 by reducing the diameter of the light beam that exited fiber 16. In this manner, the diameter of the illuminated spot on the surface of the specimen (e.g., about 20 µm) may be smaller than the diameter of the fiber. As such, the system may include a fiber optic that collects light from a light source (i.e., an illuminator), and the collected light exiting the fiber optic is directed to the surface of specimen 10 by objective 18 to control the size of the illuminated spot on the specimen. As such, the illuminated spot focused on specimen 10 may correspond to a demagnified image of the end of the fiber.

The spot focused onto the specimen by objective 18 may be scanned across the specimen by moving the specimen in one or more directions, as indicated by arrows 20. For example, the system may include a chuck (not shown) on which specimen 10 may be disposed during inspection. The chuck may include any suitable chuck known in the art. The chuck may be mounted on one or more stages (not shown) that are configured to translate the chuck and therefore the specimen disposed thereon in directions substantially perpendicularly to the surface normal. The stage(s) can be either x and y stages or a combination of radial and rotating stages. The stage(s) may include any suitable mechanical or robotic assembly known in the art.

Light specularly reflected from the spot scanned across specimen 10 may, in this embodiment, be collected by objective 18. Light collected by objective 18 may be collected and directed by fiber 16 to beam splitter 14. Beam splitter 14 may be configured to direct a substantial portion of the specularly reflected light to non-imaging detector 22. As such, in this embodiment, objective 18, fiber 16, beam splitter 14, and non-imaging detector 22 form a non-imaging detection subsystem of the system shown in FIG. 1. In this manner, the surface of specimen 10 reflects light that is collected by the objective and the fiber, a substantial portion of which is directed by the beam splitter onto the photosensitive surface of non-imaging detector 22. In some embodiments, the non-imaging detector may include a photomultiplier tube (PMT) or an avalanche photodiode (APD). Non-imaging detector 22 is configured to generate output signals responsive to light specularly reflected from the spot scanned across the specimen.

Output signals generated by the detector of the non-imaging detection subsystem may be provided to one or more electronic components coupled to the non-imaging detector. For example, analog-to-digital (A/D) converter 24 may be coupled to non-imaging detector 22. A/D converter 24 may be coupled to the non-imaging detector using any appropriate method or device known in the art. A/D converter 24 may also be coupled to processor 26 using any appropriate method or device known in the art. In this manner, processor 26 may receive the output signals generated by the non-imaging detection subsystem after the output signals have been processed by A/D converter 24.

Processor 26 is configured to generate images of specimen 10 using the output signals. For example, as the stage(s) move, the output signals of the non-imaging detector are sampled and digitized (by A/D converter 24). The digitized output signals may be stored to a storage medium (not shown) coupled to processor 26. Therefore, by sequential motion of the stage(s) and sampling of the non-imaging detector, a digital image of the surface of specimen 10 is acquired in the storage medium and may be assembled by processor 26.

Processor 26 is also configured to detect defects on the specimen using the images. Processor 26 may be configured to use any method and/or algorithm known in the art to detect defects on the specimen using the images. The defects that are detected by processor 26 may include any type of defects known in the art. Furthermore, the processor may be configured to perform any other defect related functions known in the art. Processor 26 may include any suitable processor known in the art.

Processor 26 may also be configured to control one or more components of the system shown in FIG. 1. For example, processor 26 may be coupled to the stages described above using any suitable method or device known in the art. In addition, processor 26 may be configured to control the stages to thereby control the scanning of the spot across the specimen.

The system shown in FIG. 1 has a number of advantages over other currently used bright field (BF) inspection systems. For instance, the system shown in FIG. 1 is configured to perform BF inspection of specimen 10 using a spot scanned across the specimen and non-imaging optics in a manner similar to that used in dark field (DF) spot scanning inspection systems. This optical configuration eliminates the coupling between the detector element periodicity and the detector sampling frequency required in other BF inspection systems. This decoupling eliminates one of the major limitations of macro defect inspection systems, which is the need to match the pixel size of the detector of the system to the numerical aperture (NA) of the objective. Thus, in a currently used BF inspection system configured to use a detector having a pixel size of 5 μm and, for example, 4×4 sampling of the detector requires a 20 μm equivalent point spread function, which is achieved by an imaging NA of 0.03. If the imaging NA of such a system was greater than 0.03, aliasing effects would be introduced into the images generated by the system. "Aliasing" generally refers to distortion of an image in which one or more features of a specimen do not appear in the image. Aliasing may occur when a lateral dimension and a position of the features in the image correspond to a pixel spacing of the detector.

In one embodiment, therefore, the non-imaging detection subsystem includes an objective (e.g., objective 18) and a detector (e.g., detector 22), and the NA of the objective advantageously does not match a pixel size of the detector. Since the systems described herein do not have to be configured such that the pixel size of the detector matches the NA of the objective (e.g., to eliminate aliasing), the necessity of using an objective having substantially limited NA, which results in inefficient light collection, is eliminated. Limitations on the NA of the system embodiments described herein are also reduced since the field of view of the system is substantially small, and since the system is configured essentially as a geometrical optical magnifying configuration, aberrations of the optical components of the system are irrelevant to performance of the system. In this manner, the systems described herein can have a larger imaging NA and thus more efficient light collection than currently used BF inspection systems. For example, in one embodiment, the non-imaging detection subsystem includes an objective (e.g., objective 18) having an NA of greater than about 0.05. Therefore, in some embodiments, the system includes an objective that has an NA of greater than about 0.05 that is not matched to a pixel size of the non-imaging detector. In addition, the NA of objective 18 may be equal to or greater than any reasonable value such as about 0.15, which can dramatically increase the light collection of the system beyond that achievable with an NA of 0.03 (e.g., an NA of about 0.15 corresponds to a light collection increase of about 25×).

In one embodiment, the system includes a non-imaging detector configured to detect the light collected by the objective and to generate amplified output signals responsive to the detected light. For instance, the optical configuration of the system shown in FIG. 1 advantageously allows the use of relatively high gain detectors such as PMTs and APDs. Such detectors may have a gain of about 50 or more. Using a relatively large NA as described further above in combination with a relatively high gain detector may increase the detection efficiency of the systems described herein by about 600× or more (depending on the shot noise limit) compared to the efficiency of currently used BF inspection systems.

The non-imaging detection subsystem of the system embodiments described herein may also be configured to include a non-imaging detector that has a relatively large dynamic range. The non-imaging detector may also be selected to be capable of single photon detection. Therefore, the non-imaging detection subsystems included in the embodiments described herein have a number of advantages over other currently used BF imaging detection subsystems. For instance, one example of an imaging detector commonly used in BF inspection systems is a charge coupled device (CCD). A CCD and other similar imaging detectors have a relatively small well capacity and baseline readout noise. As such, the systems described herein may have a higher signal-to-noise ratio, and therefore higher sensitivity, than currently used BF inspection systems.

The system embodiments described herein are configured to generate images of the surface of specimen 10 with moderate resolution (e.g., a resolution corresponding to a pixel size of about 5 μm to about 20 μm). In this manner, the systems may be particularly useful for macro/mezzo defect inspection applications. The system may also be configured to use the information acquired by inspection for defect detection and classification for a variety of specimens such as a patterned wafer and a non-patterned wafer. The non-patterned wafer may include a wafer having a film formed thereon (i.e., a "blanket" film formed thereon), a bare silicon wafer, or a wafer having a resist formed thereon. The film and the resist formed on the wafer may include any such materials known in the art.

The combination of the larger collection NA (without causing aliasing) and relatively large non-imaging detector gain that can be used in the system embodiments described herein is also advantageous since time delay integration (TDI) type detection is not relied upon to achieve adequate performance for at least macro/mezzo defect applications.

The system embodiments described herein are also advantageous since the burden of forming an image is transferred to the acquisition electronics (e.g., processor 26) instead of the optics of the system. Thus, the quality of the acquisition optics (e.g., objective 18) can be substantially reduced from that currently used in optical imaging based inspection systems thereby reducing the cost of the system embodiments described herein compared to other imaging systems. As such, the system embodiments described herein include a non-imaging optical configuration that is used to provide a system capable of acquiring images of a specimen using relatively inexpensive optics.

The objective may be selected based on the selected magnification of the spot on the surface of specimen 10. In addition, the system may be configured to alter a magnification of the light detected by the non-imaging detection subsystem, and therefore a magnification of the images generated by the processor using the output signals generated by the non-imaging detection subsystem, by altering the conjugate planes of the objective and the non-imaging detection subsystem. The system may be configured to alter the conjugate planes of the objective and the non-imaging detection subsystem using any method or device known in the art.

In some embodiments, the system shown in FIG. 1 is configured to alter a sampling frequency of the non-imaging detection subsystem to alter a magnification of the images generated by the processor of the system. For example, the system may be configured to control the sampling frequency of the non-imaging detection subsystem to alter the magnification of the light detected by the non-imaging subsystem and therefore the magnification of the images generated by the processor using the output signals. The system may be configured to alter and control the sampling frequency of the non-imaging detection subsystem in any manner known in the art. In this manner, the system shown in FIG. 1 may be configured to have variable magnification. In a further embodiment, the system is configured to select a sampling frequency of the non-imaging detection subsystem to substantially eliminate aliasing effects in the images. For instance, the sampling frequency of the non-imaging subsystem may be relatively high (e.g., 4 samples per optical spot) to substantially eliminate aliasing effects. The system shown in FIG. 1 may be further configured as described herein.

Figure 2:
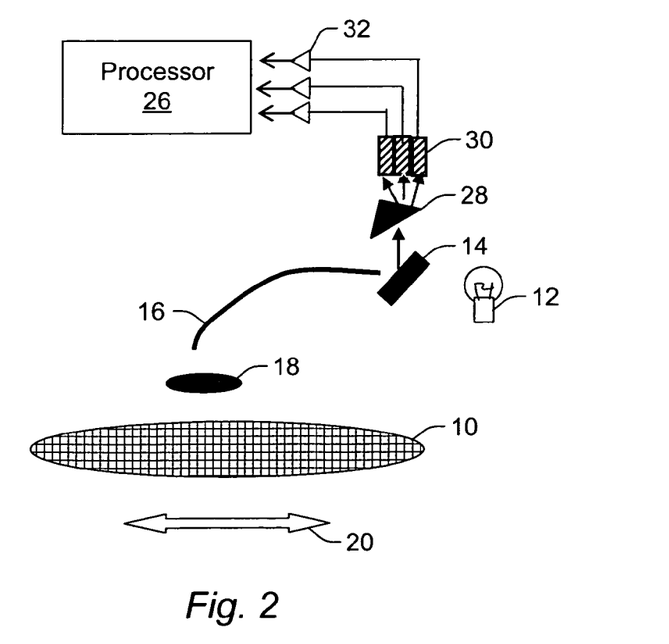

A different embodiment of a system configured to inspect a specimen is illustrated in FIG. 2. Elements shown in FIG. 2 that may be configured as described above with respect to FIG. 1 are not described further herein for the sake of brevity. In this embodiment, the illumination subsystem includes light source 12 that is a broadband light source. The broadband light source may include any suitable broadband light source known in the art. For example, the broadband light source may be a tungsten-halogen incandescent light source or an arc lamp. The broadband light source used in this embodiment may be selected to generate light with sufficiently high intensity such that additional information about the surface of the specimen may be obtained as described further herein. In this embodiment, the illumination subsystem also includes beam splitter 14, fiber 16, and objective 18, each of which may be configured as described above.

In this embodiment, light that is specularly reflected from the spot scanned across specimen 10 is collected by objective 18, collected by fiber 16, and directed by beam splitter 14 to dispersive optical component 28. Dispersive optical component 28 may be a prism, a grating, or any other suitable optical component known in the art that can be used to separate light having multiple wavelengths into spatially separated light beams having different wavelengths.

In the embodiment shown in FIG. 2, the non-imaging detector included in FIG. 1 is replaced with non-imaging detectors 30. In this manner, the detection subsystem of the system shown in FIG. 2 includes objective 18, fiber 16, beam splitter 14, dispersive optical component 28, and non-imaging detectors 30.

As shown in FIG. 2, the spectrally dispersive optical component may be inserted between the fiber that is used to collect the light specularly reflected from the spot scanned across the specimen and non-imaging detectors 30. In this manner, light having different wavelengths or wavebands may be directed to different non-imaging detectors. Each of the non-imaging detectors may be configured to generate output signals that are responsive to different wavelengths or wavebands of light specularly reflected from the spot scanned across the specimen. In this manner, the non-imaging detection subsystem is configured to simultaneously generate different output signals that are responsive to different wavelengths of the light specularly reflected from the spot scanned across the specimen.

Each of the non-imaging detectors may be coupled to one of A/D converters 32. The non-imaging detectors may be coupled to the A/D converters as described herein. In addition, each of A/D converters 32 shown in FIG. 2 is coupled to processor 26. In this manner, the output signals generated by the non-imaging detectors may be provided separately to the processor. As such, the system shown in FIG. 2 is configured for acquisition of measurements for multiple spectral bands simultaneously by using a broadband illumination source and a dispersive optical component to direct different wavelengths or wavebands of light to different non-imaging detectors of the detection subsystem.

Although the system of FIG. 2 is shown to include three different non-imaging detectors, each of which detects light specularly reflected from the spot scanned across the specimen at different wavelengths or wavebands, it is to be understood that the system shown in FIG. 2 may include two or more non-imaging detectors. In addition, the dispersive optical component may be configured to separate the specularly reflected light into two or more wavelengths or wavebands. In some embodiments, the number of different wavelengths or wavebands into which light is separated by the dispersive optical component may be equal to the number of non-imaging detectors included in the detection subsystem. In addition, the dispersive optical component may be configured to separate light specularly reflected from the spot scanned across the specimen into one or more near vacuum ultraviolet (near-VUV) wavelengths, one or more deep ultraviolet (DUV) wavelengths, one or more ultraviolet (UV) wavelengths, one or more visible wavelengths, or some combination thereof. The wavelengths or wavebands into which the light is dispersed may vary depending on, for example, the wavelengths of light used to illuminate the specimen, one or more characteristics of the specimen, one or more characteristics of defects of interest on the specimen, or some combination thereof.

The embodiment of the system shown in FIG. 2 has all of the advantages of the system of FIG. 1 described above in addition to further advantages over other currently used BF inspection systems. For instance, the system shown in FIG. 2 has a configuration that is suitable for automatic defect classification (ADC). In particular, the output signals generated for light specularly reflected from the spot scanned across the specimen at more than one wavelength or waveband may provide sufficient information such that ADC of defects detected on the specimen may be performed by the system. In one such embodiment, processor 26 is configured to perform ADC. In an additional embodiment, processor 26 is configured to determine if the defects detected on the specimen are nuisance defects. The processor may be configured to perform ADC and nuisance defect detection using any appropriate algorithm and/or method known in the art.

Monochromatic illumination and therefore monochromatic light collection can be problematic for BF inspection applications, particularly in the presence of process variations on the specimen. However, generating output signals for light specularly reflected from the spot scanned across the specimen at more than one wavelength or waveband as described herein desensitizes the inspection system to process variations that are inherent to semiconductor manufacturing processes. In one embodiment, therefore, an accuracy of the system shown in FIG. 2 is substantially independent of variations in the specimen caused by variations in a process performed on the specimen prior to inspection.

In addition, generating output signals for light specularly reflected from the spot scanned across the specimen at different wavelengths or wavebands allows the system to inspect specimens with different characteristics using wavelengths or wavebands that are appropriate for the different specimens. Therefore, for inspection of some specimens, output signals generated by fewer than all of the non-imaging detectors (i.e., for fewer than all of the detected wavelengths or wavebands) may be used for defect detection and other defect related functions.

Furthermore, as described herein, the embodiment of the system shown in FIG. 2 may include a non-imaging detector such as a PMT or APD. Therefore, the system shown in FIG. 2 utilizes broadband illumination and detection without using a TDI as a detector even for relatively small pixel sizes (e.g., pixels sizes of about 5 µm or smaller). The embodiment of the system shown in FIG. 2 may be further configured as described herein.

Figure 3:
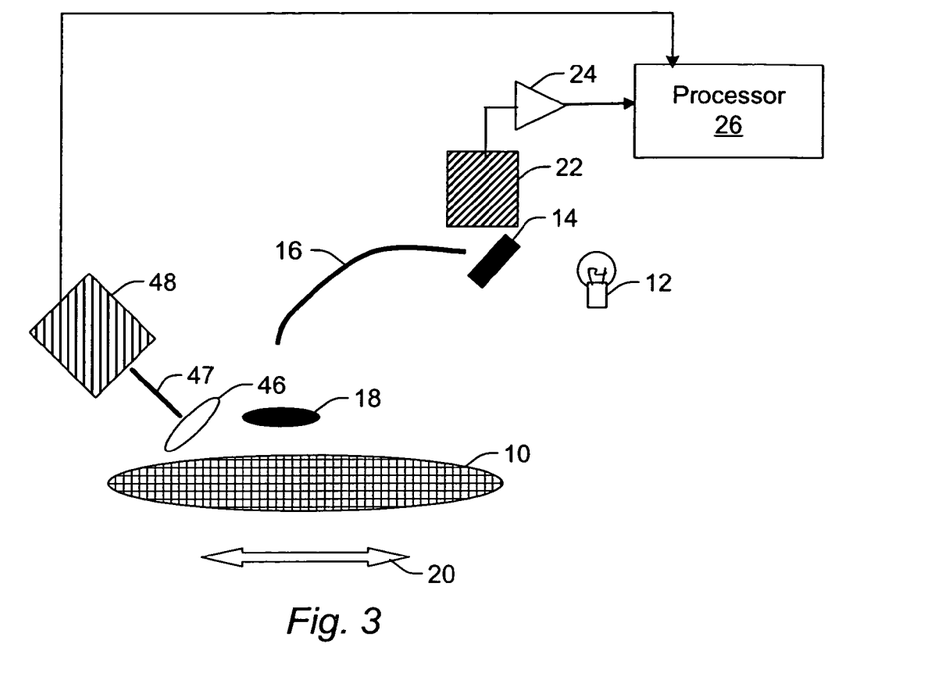

An additional embodiment of a system configured to inspect a specimen is illustrated in FIG. 3. Elements shown in FIG. 3 that may be configured as described above with respect to FIG. 1 are not described further herein for the sake of brevity. In the embodiment shown in FIG. 3, the system includes an additional non-imaging detection subsystem that is configured to generate additional output signals responsive to light scattered from the spot scanned across the specimen. In one such embodiment, processor 26 is configured to detect defects on specimen 10 using the additional output signals. In another embodiment, the non-imaging detection subsystem and the additional non-imaging detection subsystem are configured to generate output signals substantially simultaneously. In this manner, the system may be configured for BF signal collection simultaneously with DF signal collection. However, the system may be used to generate BF information only, DF information only, BF and DF information simultaneously, or BF and DF information sequentially.

As shown in FIG. 3, this embodiment of the system may include additional objective 46. Objective 46 is configured to collect light scattered from the spot scanned across the specimen. Objective 46 may include any appropriate optical component known in the art. In addition, although objective 46 is shown in FIG. 3 to be a single refractive lens, it is to be understood that the additional objective may include one or more refractive optical components or one or more reflective optical components. Objective 46 may have one or more characteristics that are the same as or different than objective 18.

Light collected by objective 46 is collected by fiber 47 that is configured to direct the light to additional non-imaging detector 48. Fiber 47 may include any of the fibers described herein. The additional non-imaging detection subsystem, therefore, includes objective 46, fiber 47, and non-imaging detector 48. The additional non-imaging detection subsystem also may or may not include fiber 47. In this manner, non-imaging detector 48 is configured to generate output signals responsive to light scattered from the spot scanned across the specimen. As such, the additional non-imaging detection subsystem is configured to generate DF signals. The output signals generated by the additional non-imaging detection subsystem may be sent to an A/D converter (not shown in FIG. 3) that may be configured as described herein.

The output of the A/D converter may be provided to processor 26. In this manner, processor 26 may be configured to generate an image of the specimen using output signals generated by non-imaging detector 48. Therefore, the processor may be configured to generate BF images and DF images of the specimen using the non-image output signals generated by the detection subsystems. In addition, the processor may be configured to use the DF information provided by non-imaging detector 48 alone or in combination with BF information provided by non-imaging detector 22 to detect defects on the specimen and to optionally perform one or more other defect related functions such as defect classification, nuisance defect identification, etc.

The DF information described above may be generated by collecting and detecting light scattered from the spot scanned across the specimen at any suitable collection angle. In addition, the angle at which the light scattered from the spot scanned across the specimen is collected and detected may be determined based on, for example, one or more characteristics of the illumination (e.g., angle of incidence, wavelength (s), polarization, etc.), one or more characteristics of the specimen, one or more characteristics of the defects of interest, or some combination thereof. In some embodiments, the system may be configured to alter the angle at which the scattered light is collected and detected, for example, by altering a position of objective 46, fiber 47, and non-imaging detector 48. The system may be configured to alter a position of objective 46, fiber 47, and non-imaging detector 48 in any manner known in the art.

In another embodiment, the system shown in FIG. 3 may include more than one non-imaging detection subsystem that are configured to detect light scattered at different angles from the spot scanned across the specimen. In this manner, the system may be configured to generate DF information at different scattering angles simultaneously. Each of the non-imaging DF detection subsystems may be coupled to a different objective or other light collecting optical component known in the art. The non-imaging DF detection subsystem or subsystems that are used for inspection of any particular specimen may be determined based on the collection angle(s) that may be selected as described above. The system shown in FIG. 3 has all of the advantages of the system shown in FIG. 1 described further above. The system shown in FIG. 3 may be further configured as described herein.

Although the systems shown in FIGS. 1-3 include fiber 16 that is configured to direct light from light source 12 to objective 18, it is to be understood that in another embodiment the fiber may be replaced with one or more other light directing optical components (not shown) such as one or more mirrors. In such embodiments, the illumination subsystem may also include an aperture (not shown) that is configured to control a size of the illumination spot directed to objective 18 and specimen 10. The aperture may include any appropriate aperture known in the art. In addition, the aperture included in the illumination subsystem may be a controllable or variable aperture. For instance, the aperture may be coupled to one or more devices (not shown) that are coupled to processor 26. The processor may be configured to control the one or more devices such that the one or more devices alter one or more dimensions of the aperture.

Although the systems shown in FIGS. 1-3 include fiber 16 configured for use in both the illumination subsystem and the non-imaging detection subsystem (i.e., for both illumination and pick up), the illumination can be delivered to the specimen in any other manner through objective 18. For instance, in a spot scanning system (and a multi-spot scanning system described further herein), the system performs imaging twice, once for imaging the spot or spots on the specimen for illumination, and once for imaging the illuminated spot(s) on the fiber (or fibers) for collection. In addition, imaging for illumination and imaging for detection are essentially independent of each other. Therefore, regardless of how the illumination is provided to the specimen, fiber 16 (or multiple fibers) is used for collecting and directing the light to the non-imaging detector or detectors. In this manner, the NA of illumination (e.g., the NA of objective 18) may be selected to be different from the NA of detection (e.g., the NA used for pick up).

The embodiments of the system shown in FIGS. 1-3 are, therefore, configured for narrowband inspection, broadband inspection, or BF and DF inspection. However, it is to be understood that the system may include various combinations of the above-described system configurations to increase the inspection capability of the system. For instance, the non-imaging DF detection subsystem shown in FIG. 3 may be included in any of the system embodiments shown in FIGS. 1-2. In this manner, two or more of the above described system configurations may be combined to provide one or more channels of information about the specularly reflected light possibly in combination with information about the scattered light. This additional information that can be generated by the system may improve the ability of the system (e.g., processor 26) to perform ADC and/or nuisance identification and rejection.

To increase the speed of inspection, a single fiber configured as described above may be replaced with an array of fibers in which individual fibers are sufficiently separated from each other (e.g., separated to sufficiently reduce cross talk between the fibers). In one such embodiment, the non-imaging detection subsystem includes two or more non-imaging detectors, instead of a single non-imaging detector. Each of the non-imaging detectors may be dedicated to a single fiber. In other words, each of the non-imaging detectors may be dedicated to generating output signals responsive to the light specularly reflected from one of the spots scanned across the specimen and collected by one of the multiple fibers.

Figure 4:
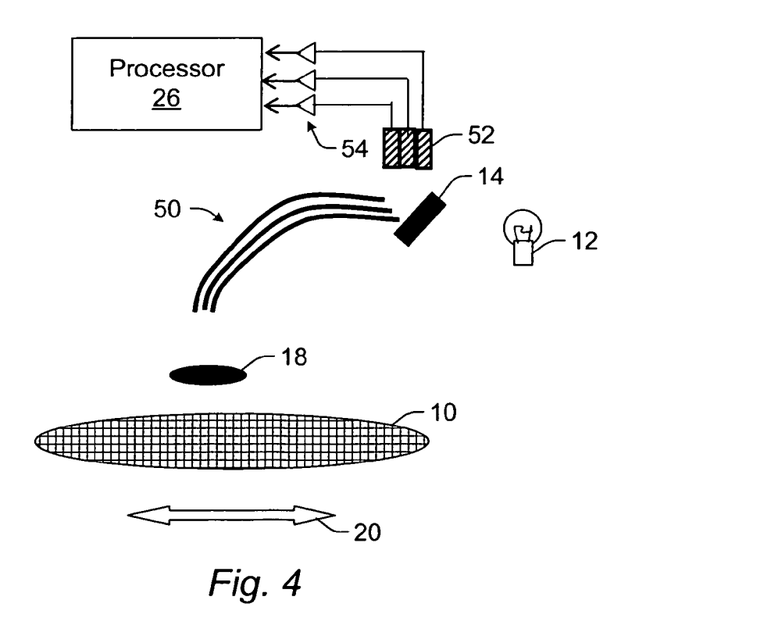

One embodiment of a system configured for relatively high speed inspection is shown in FIG. 4. In particular, the system shown in FIG. 4 is configured for relatively high speed data acquisition by parallelization of the system. Elements shown in FIG. 4 that may be configured as described above with respect to FIG. 1 are not described further herein for the sake of brevity. The illumination subsystem of the system shown in FIG. 4 is configured to illuminate the specimen by scanning multiple spots across the specimen simultaneously. For example, the illumination subsystem may include multiple fibers 50 that are configured to direct light from light source 12 (that passed through beam splitter 14) to objective 18. Although the system shown in FIG. 4 includes three fibers, it is to be understood that the system may include any appropriate number of fibers (i.e., two or more fibers). Each of the fibers may be similarly configured. In addition, each of the fibers may include any appropriate optical fiber known in the art.

In embodiments of the system that include one or more fibers used for illumination, the size of the spot or spots scanned across the specimen is limited by the relatively small effective NA of the fiber(s). The effect of the NA of the fiber(s) on the spot size may be mitigated by including microlenses coupled to (e.g., cemented to) the ends of the fiber(s). In addition, the effect that the fiber(s) have on the spot size may be further mitigated by reducing the working distances of the microlenses such that they are positioned in relatively close proximity to the surface of the specimen. The microlenses that are coupled to the fiber(s) may include any appropriate such lenses known in the art. Embodiments of the system that include such microlenses may or may not include objective 18.

Objective 18 is configured to focus the light from each of the multiple fibers onto specimen 10. In this manner, fibers 50 and objective 18 are configured to illuminate multiple spots on the specimen simultaneously. The multiple spots may be scanned across the specimen simultaneously as described above. The multiple spots may also be spatially separated from each other across the specimen.

Light specularly reflected from each of the spots scanned across the specimen may be collected by objective 18. Objective 18 may also be configured to direct light from each of the spots scanned across the specimen to different fibers 50. As such, each of the fibers collects light specularly reflected from a corresponding spot on the specimen. In this manner, specularly reflected light from each of the spots may be separately collected by the objective and the fibers and separately directed to beam splitter 14 by fibers 50. Beam splitter 14 is configured to direct a substantial portion of the light from each of the fibers to non-imaging detectors 52.

In this embodiment, the non-imaging detection subsystem includes objective 18, fibers 50, beam splitter 14, and non-imaging detectors 52. The number of non-imaging detectors included in the detection subsystem may be equal to the number of fibers 50 included in the system. In this manner, each of the non-imaging detectors may be dedicated to generating output signals responsive to the light collected by one of the fibers. Therefore, the light specularly reflected from different spots scanned across the specimen may be separately detected by the non-imaging detection subsystem. In one embodiment, therefore, the non-imaging detection subsystem is configured to simultaneously generate output signals responsive to light specularly reflected from the multiple spots scanned across the specimen. As such, the system shown in FIG. 4 is configured for multi-spot illumination of the specimen and multi-channel detection of light reflected from the specimen. Non-imaging detectors 52 may include any of the detectors described herein. In some embodiments of the system that include multiple fibers, one or more parameters of the non-imaging detectors such as gain and offset may be calibrated to account for differences in the optical transmission and light collection characteristics of the different fibers.

Each of the non-imaging detectors may be coupled to one of multiple A/D converters 54. A/D converters 54 may be configured as described herein. In this manner, output signals from each of the non-imaging detectors may be separately provided to processor 26, which may be configured as described herein. The system shown in FIG. 4 may be further configured as described herein.

The system shown in FIG. 4 has all of the advantages of the system of FIG. 1 described further above in addition to other advantages over currently used BF inspection systems. For instance, the image is formed by the system shown in FIG. 4 independent of the NA of the objective. Instead, the individual fibers act essentially like multiple spots, and the image can be generated pixel by pixel by the processor. Thus, the collection NA can be dramatically larger than that normally used in relatively large pixel BF inspection systems. In addition, the field of view of the system shown in FIG. 4 is substantially small compared to that of currently used BF imaging systems. In this manner, the system shown in FIG. 4 can be configured to include relatively inexpensive optical components. Furthermore, the output of each fiber can be detected using a non-imaging detector such as a PMT or an APD. These detectors have a relatively large gain thereby enhancing the sensitivity of the system. Moreover, the spot size of the system shown in FIG. 4 is determined by the image of the fiber aperture (or fiber exit) imaged on the specimen. In this manner, the system may be configured to have a continuously variable pixel size using different magnification ratios. The system shown in FIG. 4 also can advantageously be configured for simultaneous BF and DF inspection as described further herein.

Figure 5:
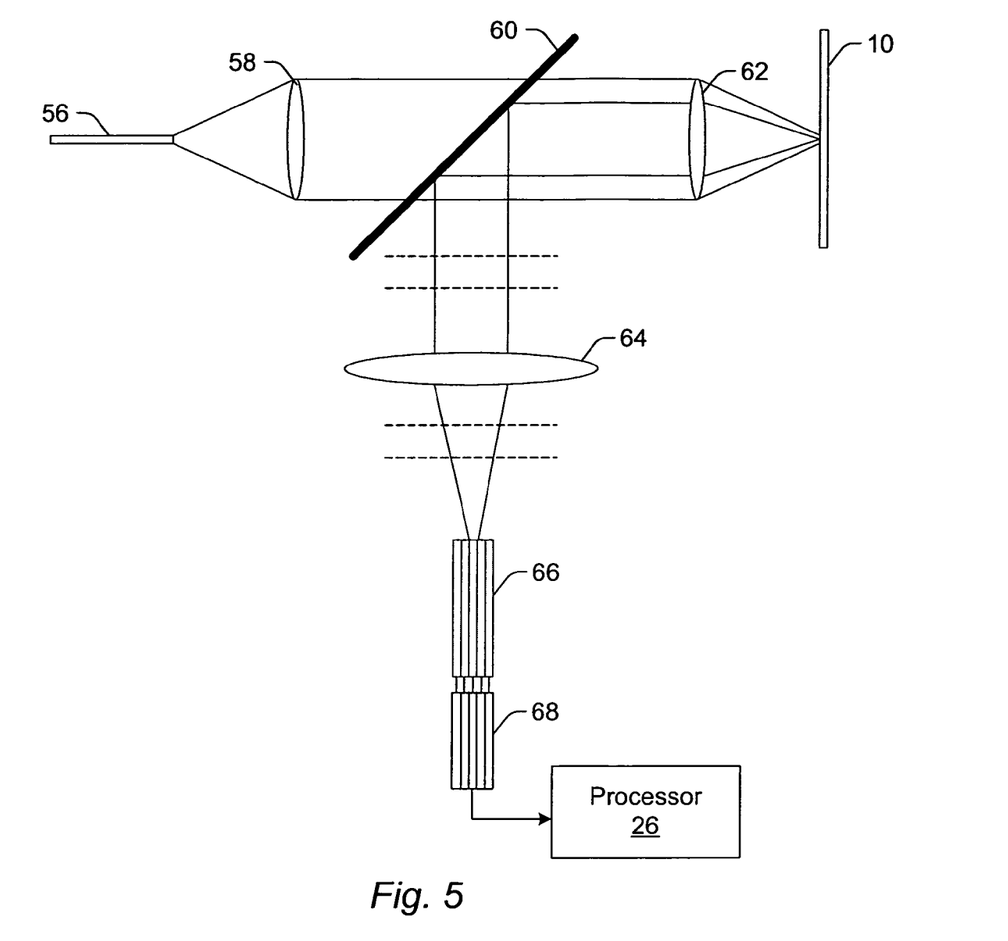

FIG. 5 illustrates a different embodiment of a system configured to inspect a specimen. The system shown in FIG. 5 is configured to illuminate a specimen by scanning a relatively large spot across the specimen and to detect light specularly reflected from different areas within the spot scanned across the specimen. The illumination subsystem of the system shown in FIG. 5 includes light source 56. Light source 56 may be an illumination rod or any other appropriate light source known in the art. In addition, light source 56 may be a narrowband light source or a broad band light source.

The illumination subsystem also includes optical component 58 and beam splitter 60. Light generated by light source 56 is directed by optical component 58 through beam splitter 60. Optical component 58 may include any appropriate optical component known in the art. In addition, although optical component 58 is shown in FIG. 5 to include one refractive lens, it is to be understood that optical component 58 may include one or more refractive lenses and/or one or more reflective optical components. Beam splitter 60 may include any appropriate beam splitter known in the art.

The illumination subsystem also includes objective 62. Objective 62 is configured to focus light that has passed through beam splitter 60 onto specimen 10. In some embodiments, objective 62 is configured to control a size of the spot on the specimen. Objective 62 may be further configured as described herein. The illumination subsystem of the embodiment shown in FIG. 5 is, therefore, different than the illumination subsystems of other system embodiments described herein in that the illumination subsystem shown in FIG. 5 does not include a fiber. In one embodiment, therefore, the illumination subsystem is configured to illuminate the specimen by flood illumination. In this manner, the size of the spot that is scanned across the specimen is not limited by the relatively small effective NA of a fiber. As such, the size of the spot that is scanned across the specimen by the illumination subsystem shown in FIG. 5 may be relatively large (e.g., about 1 mm or greater). The illumination subsystem of the system shown in FIG. 5 may be configured to scan the spot across the specimen as described herein.

The system shown in FIG. 5 also includes a non-imaging detection subsystem that is configured to generate output signals responsive to light specularly reflected from the spot scanned across the specimen. For instance, the non-imaging detection subsystem includes objective 62 and beam splitter 60. Objective 62 is configured to collect the light specularly reflected from the spot scanned across the specimen. Light collected by objective 62 is directed to beam splitter 60.

A substantial portion of the light collected by objective 62 is directed by beam splitter 60 to optical component 64 that is also included in the non-imaging detection subsystem. Optical component 64 is configured to focus the light from beam splitter 60 to array of fibers 66. Optical component 64 may include any appropriate optical component known in the art. In addition, although optical component 64 is shown in FIG. 5 to include one refractive lens, it is to be understood that optical component 64 may include one or more refractive optical components and/or one or more reflective optical components.

Array of fibers 66 includes multiple fibers, each of which is configured to direct light to a dedicated non-imaging detector such as one of non-imaging detector array 68. In this manner, the system shown in FIG. 5 is configured for single spot illumination and multi-channel detection. The fibers and the non-imaging detectors may include any of the fibers and non-imaging detectors described herein. Furthermore, the non-imaging detection subsystem may include any appropriate number of fibers and non-imaging detectors. Alternatively, non-imaging detector array 68 may be replaced by a multi-channel non-imaging detector. For example, the non-imaging detector may include a multi-anode PMT or any other appropriate multi-channel non-imaging detector known in the art. The multi-channel non-imaging detector may include any appropriate number of channels known in the art.

As described above, the illumination subsystem shown in FIG. 5 is configured to illuminate the specimen by flood illumination. In this manner, in the system of FIG. 5, the specimen is flood illuminated, and the magnified image of the sample is projected onto an array of fibers, a two-dimensional array of non-imaging detectors, or a two-dimensional multi-channel array of a non-imaging detector. In one such embodiment, array of fibers 66 is configured to collect the light specularly reflected from different portions of the spot scanned across the specimen. In this manner, light specularly reflected from different areas within the spot scanned across the specimen may be separately detected. Each of the different areas has a size that is smaller than the size of the spot scanned across the specimen. In addition, the non-imaging detector array or the multi-channel non-imaging detector is configured to generate output signals responsive to light specularly reflected from different areas within the spot scanned across the specimen. The different areas within the spot scanned across the specimen from which specularly reflected light is detected may be spatially separated from each other.

As described above, the illumination subsystem of the system shown in FIG. 5 may include a broadband light source. In one such embodiment, each of the output signals generated by the non-imaging detection subsystem is responsive to multiple wavelengths of the light specularly reflected from the spot scanned across the specimen. In other words, the system may utilize broadband illumination, and the collected light may not be split into separate beams based on wavelength as described above with respect to the system shown in FIG. 2. In this case, all of the light across the broadband spectrum collected by each fiber is detected by a single detector dedicated to each fiber to provide a single output per fiber channel.

Each non-imaging detector or each channel of the multi-channel non-imaging detector may be coupled to a dedicated A/D converter (not shown in FIG. 5). The A/D converters may be configured as described herein. In addition, the A/D converters may be coupled to processor 26. In this manner, the output signals generated by the detector or detectors may be processed by the A/D converters and provided to processor 26. In this manner, processor 26 may separately receive output signals from each non-imaging detector or each channel of the multi-channel non-imaging detector. Processor 26 is configured to generate images of the specimen using the output signals. Processor 26 is also configured to detect defects on the specimen using the images. Processor 26 may be further configured as described herein. The system shown in FIG. 5 may be further configured as described herein. In addition, the system shown in FIG. 5 has all of the advantages of the systems shown in FIGS. 1 and 4 described above.

Figure 6:
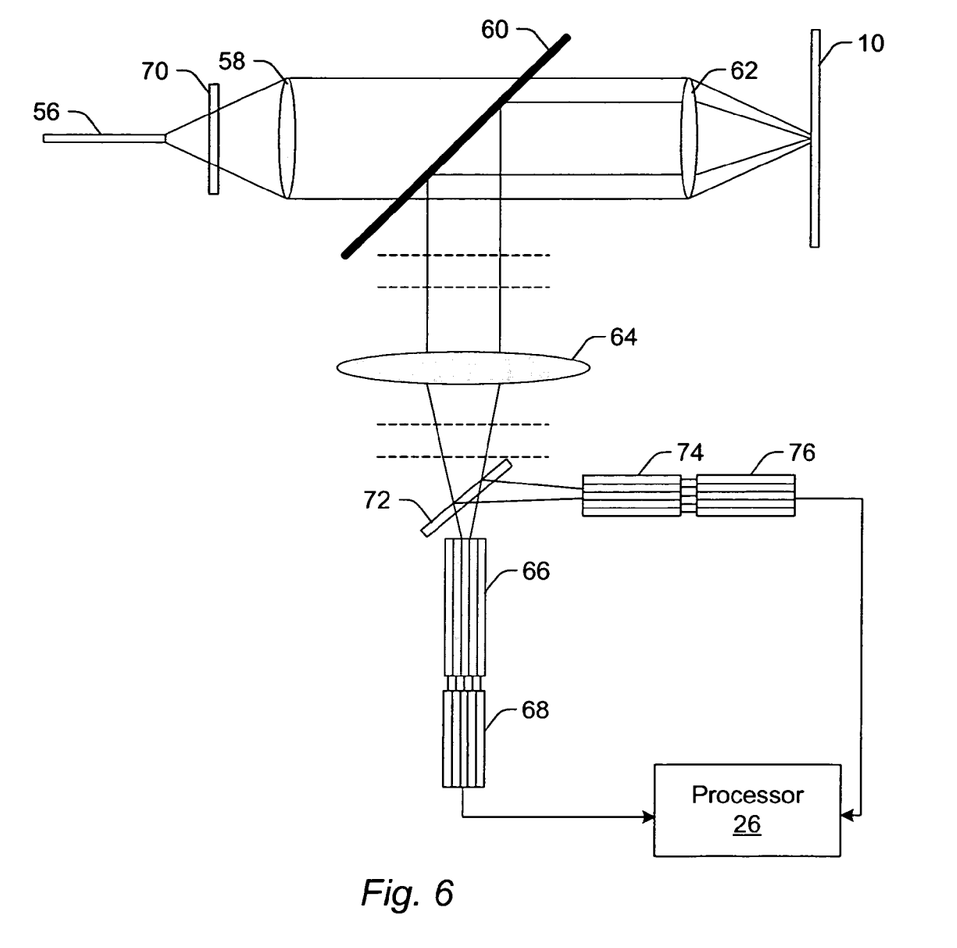

Another embodiment of a system configured to inspect a specimen is illustrated in FIG. 6. Elements shown in FIG. 6 that may be configured as described above with respect to FIG. 5 are not described further herein for the sake of brevity. In this embodiment, the system is configured to direct light having different polarizations into different detection channels to obtain additional information about the light specularly reflected from the spot scanned across specimen 10. This additional information may be utilized to perform ADC with higher accuracy.

In the embodiment shown in FIG. 6, light from light source 56 is directed to polarizer 70. Polarizer 70 may include any appropriate polarizing component known in the art. In addition, the polarizing component may be selected based on the polarization of light generated by light source 56 and the polarization selected for illumination of specimen 10. In some embodiments, the system may be configured to illuminate different specimens with light having different polarizations. For example, in one embodiment, the system may be configured to alter a position of polarizer 70 (e.g., by rotating polarizer 70) such that linearly polarized light having different orientations may be used for illumination. In another embodiment, the system may include more than one polarizer (not shown), each of which have one or more different characteristics. In this manner, the polarizer that is positioned in the optical path of the system may be selected based on the selected polarization for the illumination. In a similar manner, a polarizer may or may not be positioned in the optical path of the system depending on the polarization selected for illumination. The system may be configured to alter a position of polarizer 70 or to alter the polarizer disposed in the illumination path in any manner known in the art. In this manner, the system is configured to use polarized light for illumination and polarization specific information about the specimen for defect detection and possibly other functions such as defect classification.

Light that passes through polarizer 70 is directed by optical component 58 through beam splitter 60. Objective 62 focuses light that has passed through beam splitter 60 onto specimen 10. Objective 62 is also configured to collect the light specularly reflected from the spot scanned across the specimen. Light collected by objective 62 is directed to beam splitter 60. A substantial portion of the light collected by objective 62 is directed by beam splitter 60 to optical component 64. Optical component 64 is configured to focus the light from beam splitter 60 to optical component 72. Optical component 72 is configured to split the light from optical component 64 into light beams having different polarizations. Optical component 72 may be a polarizing beam splitter, a birefringent optical component, or any other suitable optical component known in the art.

In one embodiment, the system shown in FIG. 6 includes two non-imaging detection subsystems that are configured to generate output signals responsive to light specularly reflected from the spot scanned across the specimen. For example, light beams having different polarizations are produced by optical component 72 and directed to array of fibers 66 and array of fibers 74. Array of fibers 66 is coupled to non-imaging detector array 68 as described further above. In addition, array of fibers 74 is coupled to non-imaging detector array 76. Array of fibers 74 may be configured as described further above. Non-imaging detector array 76 may be configured as described above and may be replaced with a multi-channel non-imaging detector as described above.

The output signals generated by non-imaging detector arrays 68 and 76 are responsive to light having different polarizations. In this manner, the output signals generated by non-imaging detector arrays 68 and 76 contain information about the polarization of the light specularly reflected from the spot scanned across the specimen. The output signals generated by non-imaging detector arrays 68 and 70 may be processed by A/D converters (not shown) coupled to the arrays. The A/D converters may be configured as described herein. In this manner, output signals that contain information about the polarization of the light specularly reflected from the spot scanned across the specimen may be provided to processor 26. Processor 26 may use this information to detect defects on the specimen and optionally to perform one or more other functions such as classifying defects detected on the specimen. The embodiment of the system shown in FIG. 6 has all of the advantages of the systems described above. The system shown in FIG. 6 may be further configured as described herein.

Figure 7:
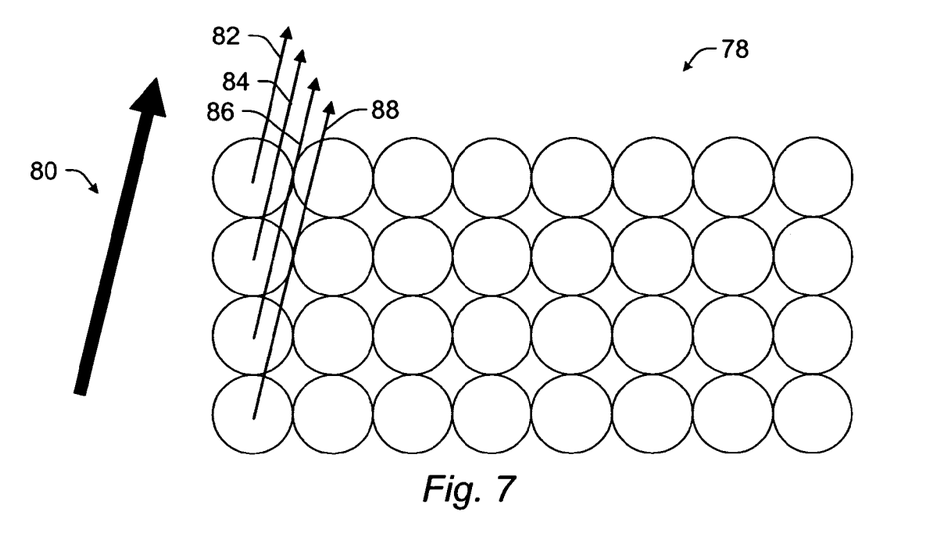
FIG. 7 is a schematic diagram illustrating a cross-sectional view of one embodiment of an array of fibers that may be included in the system embodiments described herein.

The systems shown in FIGS. 4-6 may include a non-imaging detection subsystem having a one-dimensional or two-dimensional configuration. For example, as shown in FIG. 7, one embodiment of array 78 of fibers that may be included in the system embodiments described herein is configured as a two-dimensional array of fibers. In systems that include such an array of fibers, the non-imaging detectors or channels (not shown in FIG. 7) may or may not be similarly arranged in an array. For instance, if the two-dimensional array of fibers is only used to collect the light specularly reflected from the specimen (as opposed to being used for both illumination and collection), the two-dimensional array of fibers may be arranged as shown in FIG. 7 proximate the end of the fibers in which the collected light enters the fibers. However, the other end of the fibers may be arranged in any suitable configuration depending on the degree to which the fibers can be manipulated along their lengths. In this manner, the array of fibers may have a configuration different than that shown in FIG. 7 proximate the end of the fibers that the collected light exits.

As shown in FIG. 7, the light specularly reflected from a specimen (not shown in FIG. 7) may be scanned across array 78 in the direction shown by arrow 80. As further shown in FIG. 7, the position of "tracks" 82, 84, 86, and 88 relative to the scan direction ensures proper sampling of the non-imaging detectors or the channels of the multi-channel non-imaging detector configured to detect light exiting array 78 in one direction. In the other direction (i.e., the scan direction), proper sampling may be ensured through time-domain sampling of the electronic signals generated by the non-imaging detectors or the channels of the multi-channel non-imaging detector. Although array 78 is shown in FIG. 7 as a 4×8 arrangement of fibers, it is to be understood that the array of fibers may include any appropriate number of fibers in both dimensions. In addition, the fibers included in array 78 may include any of the fibers described herein.

Figure 8:
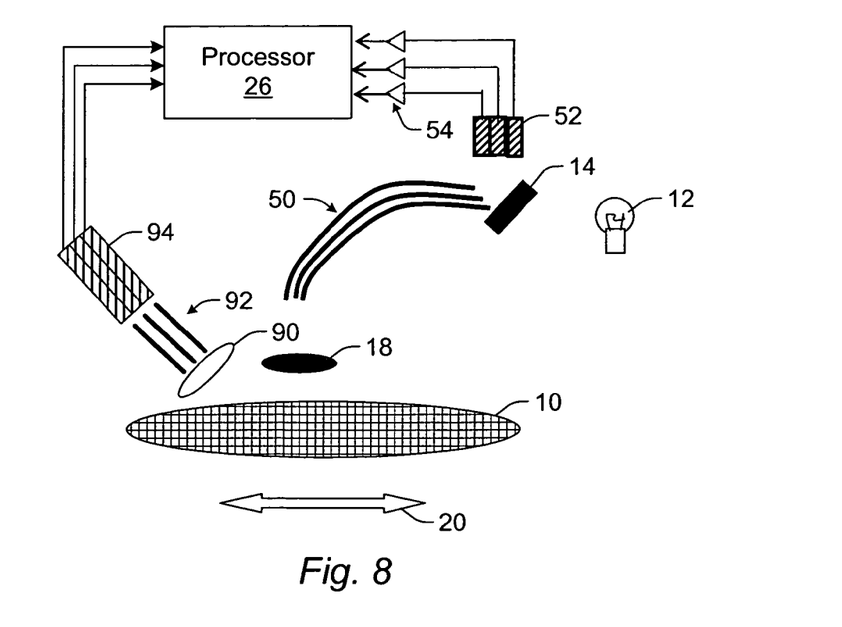
FIG. 8 is a schematic diagram illustrating a side view of an additional embodiment of a system configured to inspect a specimen.

The multi-spot BF systems shown in FIGS. 4-6 may also be configured as multi-spot DF systems. In this manner, the systems described herein may be configured to perform multi-spot BF and DF inspection in parallel. FIG. 8 illustrates one embodiment of a system configured to perform simultaneous BF and DF multi-spot data acquisition. Elements shown in FIGS. 4 and 8 that may be similarly configured will not be described further herein for the sake of brevity.

As shown in FIG. 8, the illumination subsystem is configured to illuminate the specimen by scanning multiple spots across the specimen simultaneously. The illumination subsystem may be further configured as described herein. In one embodiment, the system includes objective 90 that is configured to collect light scattered from the multiple spots scanned across the specimen. Objective 90 may be further configured as described herein. Objective 90 may be configured to direct the light scattered from the multiple spots scanned across the specimen to fibers 92. In this manner, light scattered from each of the multiple spots may be directed to a dedicated fiber. Fibers 92 may be further configured as described herein.

This embodiment of the system also includes additional non-imaging detectors 94 that are configured to simultaneously generate additional output signals responsive to light scattered from the multiple spots scanned across the specimen. In particular, additional non-imaging detectors 94 may be configured to generate output signals responsive to the light scattered from the multiple spots scanned across specimen 10 that is collected by objective 90 and fibers 92. Non-imaging detectors 94 may be further configured as described herein. The embodiment of the system shown in FIG. 8, therefore, includes an additional non-imaging detection subsystem that includes objective 90, fibers 92, and non-imaging detectors 94. In another embodiment, a multi-channel non-imaging detector may be used instead of non-imaging detectors 94.

In some embodiments, the DF non-imaging detection subsystem included in the system shown in FIG. 8 may be further configured as described in U.S. patent application Ser. No. 11/158,440 by Kadkly et al. and Ser. No. 11/158,441 by Kadkly et al., both of which were filed on Jun. 22, 2005 and are incorporated by reference as if fully set forth herein. In some embodiments, the system shown in FIG. 8 may include an additional illumination subsystem configured to provide illumination for the DF non-imaging multi-spot inspection. The additional illumination subsystem may be configured as described in the above referenced patent applications.

In one embodiment, the additional non-imaging detection subsystem is configured to generate output signals while the non-imaging detection subsystem is generating output signals. In this manner, the system shown in FIG. 8 may be configured and used for simultaneous multi-spot BF and DF inspection.

In some embodiments, non-imaging detectors 94 may be coupled to A/D converters (not shown in FIG. 8), each of which is dedicated to processing the output signals generated by one of the non-imaging detectors. In a similar manner, each of the A/D converters may be dedicated to processing the output signals generated by one of the channels of the non-imaging detector. The A/D converters may be further configured as described herein. The A/D converters may be configured to provide the processed output signals to processor 26. Processor 26 is configured to generate images of the specimen using the output signals. Processor 26 is also configured to detect defects on specimen 10 using these images. Processor 26 may be further configured as described herein.

Although the system shown in FIG. 8 includes different objectives for separately collecting light specularly reflected and scattered from the spots scanned across the specimen, it is to be understood that the system may include one objective (not shown) that is configured to collect both light specularly reflected and scattered from the spots scanned across the specimen. In this manner, the objective may be shared by the BF non-imaging detection subsystem and the DF non-imaging detection subsystem.

In one such embodiment, the BF non-imaging detection subsystem may include a notch filter that is configured to eliminate the illumination wavelength (e.g., the laser wavelength) from the light collected and detected by the BF non-imaging detection subsystem. In addition, the DF non-imaging detection subsystem may include one or more bandpass filters configured to eliminate wavelengths other than the illumination wavelength(s) from the light collected and detected by the DF non-imaging detection subsystem. The system shown in FIG. 8 may be further configured as described herein. In addition, the embodiment of the system shown in FIG. 8 has all of the advantages of the systems shown in FIGS. 1 and 4.

Figure 9:
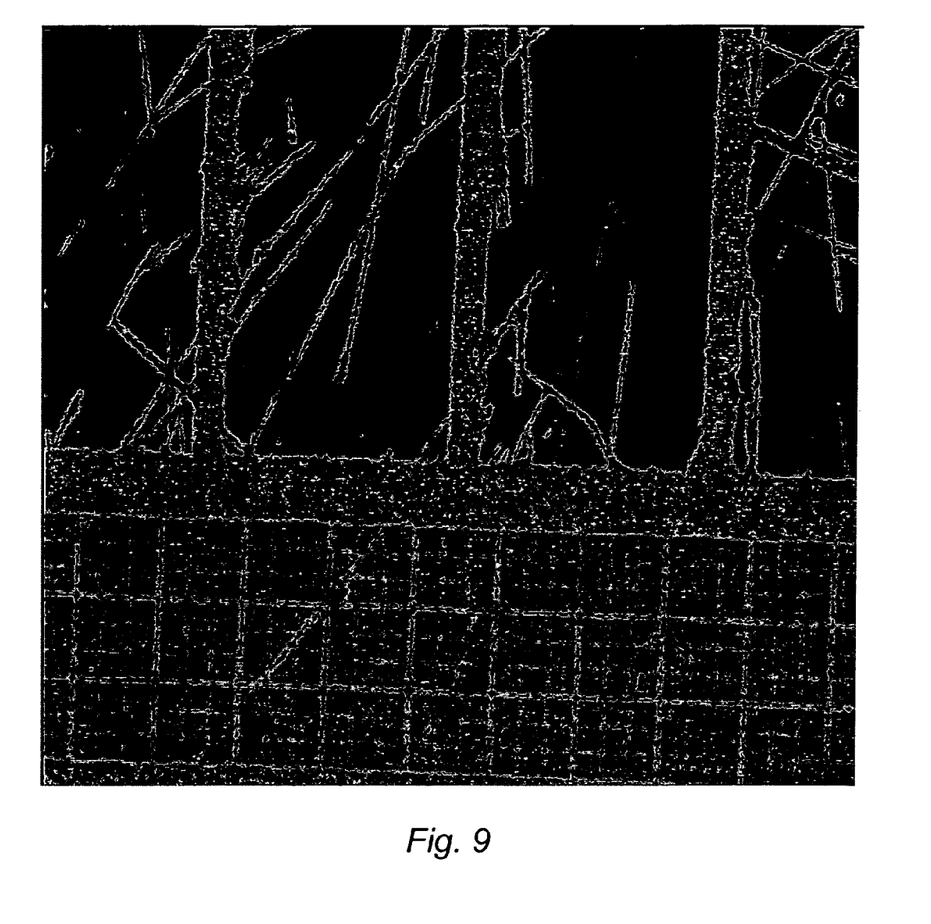
FIG. 9 is an example of an image of a specimen generated using a single fiber and white light illumination that demonstrates the operation of the system embodiments described herein.

FIG. 9 is an image of a specimen, which in this example is a patterned wafer, generated using a white light source to illuminate the specimen as described herein. Light from the white light source illuminated the specimen by scanning a spot on the specimen using a single fiber. Light specularly reflected from the specimen was directed from the specimen to a detector by the single fiber. The image was generated as described herein (e.g., from output signals generated by a non-imaging detection subsystem).

As shown in FIG. 9, the image is a relatively moderate quality image of the specimen formed at a resolution that is suitable for macro and/or mezzo defect inspection. As such, the image shown in FIG. 9 illustrates that the systems described herein can be used for inspection of a specimen as described further herein. Multiple optical fibers may be used to produce essentially this same image of the specimen through reconstruction of the output signals generated for the light exiting each multiple optical fiber. Such reconstruction may be performed by a processor that may be configured as described herein.

Additional embodiments relate to a method for inspecting a specimen. The method includes illuminating the specimen by scanning a spot across the specimen. Illuminating the specimen may be performed as described herein. The method also includes generating non-image output signals responsive to light specularly reflected from the spot scanned across the specimen. Generating the non-image output signals may be performed as described herein. In addition, the method includes generating images of the specimen using the non-image output signals. Generating the images may be performed as described herein. The method further includes detecting defects on the specimen using the images. Detecting the defects may be performed as described herein.

The method described above may be performed by any of the system embodiments described herein. In addition, the method described above may include any other step(s) described herein. For instance, in one embodiment, the method includes selecting a sampling frequency of a non-imaging detection subsystem used for generating the non-image output signals to substantially eliminate aliasing effects in the images.

In an additional embodiment, generating the non-image output signals includes simultaneously generating different non-image output signals that are responsive to different wavelengths of the light specularly reflected from the spot scanned across the specimen. In another embodiment, the method includes ADC of defects detected on the specimen. In some embodiments, an accuracy of the method is substantially independent of variations in the specimen caused by variations in a process performed on the specimen prior to inspecting the specimen. In a further embodiment, the method includes determining if the defects detected on the specimen are nuisance defects.

In some embodiments, illuminating the specimen includes illuminating the specimen by scanning multiple spots across the specimen simultaneously. In one such embodiment, generating the non-image output signals includes generating non-image output signals responsive to light specularly reflected from the multiple spots scanned across the specimen. In another such embodiment, the method includes generating additional non-image output signals responsive to light scattered from the multiple spots scanned across the specimen. Such a method may also include detecting defects on the specimen using the additional non-image output signals. In an additional embodiment, the method includes generating the non-image output signals and the additional non-image output signals substantially simultaneously.

In another embodiment, the method includes generating additional non-image output signals responsive to light scattered from the spot scanned across the specimen. In one such embodiment, the method includes detecting defects on the specimen using the additional non-image output signals. In another such embodiment, the method includes generating the non-image output signals and the additional non-image output signals substantially simultaneously.

In a further embodiment, the method includes generating additional non-image output signals responsive to light specularly reflected from the spot scanned across the specimen. The non-image output signals and the additional non-image output signals are responsive to light having different polarizations. In some embodiments, the specimen includes a patterned wafer or a non-patterned wafer. The non-patterned wafer may include a wafer having a film formed thereon, a bare silicon wafer, or a wafer having a resist formed thereon. Each of the embodiments of the method described above may include any other step(s) described herein. In addition, each of the embodiments of the method described above have advantages of the system embodiments described herein that may be used to perform the embodiments of the method.

Further modifications and alternative embodiments of various aspects of the invention may be apparent to those skilled in the art in view of this description. For example, systems and methods for inspection of a specimen are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to inspect a specimen, comprising:
    an illumination subsystem configured to illuminate the specimen by scanning a spot across the specimen;
    a non-imaging detection subsystem configured to generate output signals responsive to light specularly reflected from the spot scanned across the specimen, wherein the non-imaging detection subsystem comprises an objective and a detector, and wherein a numerical aperture of the objective is not coupled to a pixel size of the detector; and
    a processor configured to generate images of the specimen using the output signals and to detect defects on the specimen using the images.

2. The system of claim 1, wherein the numerical aperture of the objective is greater than about 0.05.

3. The system of claim 1, wherein the system is further configured to alter a sampling frequency of the non-imaging detection subsystem to alter a magnification of the images.

4. The system of claim 1, wherein the system is further configured to select a sampling frequency of the non-imaging detection subsystem to substantially eliminate aliasing effects in the images.

5. The system of claim 1, wherein the detector comprises an avalanche photodiode or a photomultiplier tube.

6. The system of claim 1, wherein the illumination subsystem comprises a narrowband light source.

7. The system of claim 1, wherein the illumination subsystem comprises a broadband light source, and wherein the non-imaging detection subsystem is further configured to simultaneously generate different output signals responsive to different wavelengths of the light specularly reflected from the spot scanned across the specimen.

8. The system of claim 1, wherein the illumination subsystem comprises a broadband light source, and wherein each of the output signals is further responsive to multiple wavelengths of the light specularly reflected from the spot scanned across the specimen.

9. The system of claim 1, wherein the illumination subsystem is further configured to illuminate the specimen by flood illumination, and wherein the non-imaging detection subsystem further comprises an array of fibers configured to collect the light specularly reflected from different portions of the spot scanned across the specimen.

10. The system of claim 1, wherein the processor is further configured to perform automatic defect classification.

11. The system of claim 1, wherein an accuracy of the system is substantially independent of variations in the specimen caused by variations in a process performed on the specimen prior to inspection.

12. The system of claim 1, wherein the processor is further configured to determine if the defects are nuisance defects.

13. The system of claim 1, wherein the illumination subsystem comprises a fiber configured to direct light from a light source to an objective, and wherein the objective is configured to focus light from the fiber onto the specimen and to control a size of the spot on the specimen.

14. The system of claim 1, wherein the illumination subsystem is further configured to illuminate the specimen by scanning multiple spots across the specimen simultaneously, and wherein the non-imaging detection subsystem is further configured to simultaneously generate output signals responsive to light specularly reflected from the multiple spots scanned across the specimen.

15. The system of claim 1, further comprising an additional non-imaging detection subsystem configured to generate additional output signals responsive to light scattered from the spot scanned across the specimen, wherein the processor is further configured to detect the defects on the specimen using the additional output signals.

16. The system of claim 1, further comprising an additional non-imaging detection subsystem configured to generate additional output signals responsive to light scattered from the spot scanned across the specimen, wherein the non-imaging detection subsystem and the additional non-imaging detection subsystem are further configured to generate the output signals and the additional output signals substantially simultaneously.

17. The system of claim 1, wherein the illumination subsystem is further configured to illuminate the specimen by scanning multiple spots across the specimen simultaneously, wherein the system further comprises an additional non-imaging detection subsystem configured to simultaneously generate additional output signals responsive to light scattered from the multiple spots scanned across the specimen, and wherein the processor is further configured to detect the defects on the specimen using the additional output signals.

18. The system of claim 17, wherein the additional non-imaging detection subsystem is further configured to generate the additional output signals while the non-imaging detection subsystem is generating the output signals.

19. The system of claim 1, further comprising an additional non-imaging detection subsystem configured to generate additional output signals responsive to light specularly reflected from the spot scanned across the specimen, wherein the output signals and the additional output signals are further responsive to light having different polarizations.

20. The system of claim 1, wherein the specimen comprises a patterned wafer or a non-patterned wafer, and wherein the non-patterned wafer comprises a wafer having a film formed thereon, a bare silicon wafer, or a wafer having a resist formed thereon.

21. The system of claim 1, wherein the images are generated by the processor independent of the numerical aperture of the objective.

22. A system configured to inspect a specimen, comprising:
- an illumination subsystem configured to illuminate the specimen by scanning a spot across the specimen;
- an objective configured to collect light specularly reflected from the spot scanned across the specimen, wherein a numerical aperture of the objective is greater than about 0.05;
- a non-imaging detector configured to detect the light collected by the objective and to generate amplified output signals responsive to the detected light, wherein the numerical aperture of the objective is not coupled to a pixel size of the non-imaging detector; and
- a processor configured to generate images of the specimen using the amplified output signals and to detect defects on the specimen using the images.

23. A method for inspecting a specimen, comprising:
- illuminating the specimen by scanning a spot across the specimen;
- generating non-image output signals responsive to light specularly reflected from the spot scanned across the specimen using a non-imaging detection subsystem, wherein the non-imaging detection subsystem comprises an objective and a detector, and wherein a numerical aperture of the objective is not coupled to a pixel size of the detector;
- generating images of the specimen using the non-image output signals; and
- detecting defects on the specimen using the images.

* * * * *